(12) United States Patent
Gregan et al.

(10) Patent No.: US 8,193,184 B2
(45) Date of Patent: Jun. 5, 2012

(54) SUBSTITUTED SULPHONAMIDES, PROCESS FOR THEIR PREPARATION, PHARMACEUTICAL COMPOSITION COMPRISING THEREOF AND THEIR USE

(75) Inventors: Fridrich Gregan, Bratislava (SK); Milan Remko, Bratislava (SK); Elena Sluciakova, Bratislava (SK); Jarmila Knapikova, Bratislava (SK)

(73) Assignee: Unimed Pharma, SPOL, S.R.O., Bratislava (SK)

( * ) Notice: Subject to any disclaimer, the term of this patent is extended or adjusted under 35 U.S.C. 154(b) by 291 days.

(21) Appl. No.: 12/596,820

(22) PCT Filed: Apr. 20, 2008

(86) PCT No.: PCT/SK2008/050005
§ 371 (c)(1),
(2), (4) Date: Dec. 31, 2009

(87) PCT Pub. No.: WO2008/130332
PCT Pub. Date: Oct. 30, 2008

(65) Prior Publication Data
US 2010/0125076 A1 May 20, 2010

(30) Foreign Application Priority Data
Apr. 20, 2007 (SK) .................................. 0054-2007

(51) Int. Cl.
C07D 207/12 (2006.01)
C07D 207/14 (2006.01)
C07D 211/22 (2006.01)
C07D 211/40 (2006.01)
C07C 311/16 (2006.01)
A61K 31/18 (2006.01)
A61K 31/40 (2006.01)
A61K 31/44 (2006.01)
A61K 31/5375 (2006.01)

(52) U.S. Cl. ..................... 514/238.2; 514/428; 514/602; 514/603; 514/331; 514/604; 548/566; 564/85; 564/86; 564/82; 544/159; 546/246; 546/248

(58) Field of Classification Search .................... None
See application file for complete search history.

(56) References Cited

FOREIGN PATENT DOCUMENTS
WO   WO 2006014134 A1 * 2/2006
* cited by examiner

*Primary Examiner* — Kamal Saeed
*Assistant Examiner* — Michael Barker
(74) *Attorney, Agent, or Firm* — Ohandt, Greeley, Ruggiero & Perle, L.L.P.; George W. Rauchfuss, Jr.

(57) ABSTRACT

Substituted sulphonamides having the general formula (I) and salts, hydrates and solvates thereof were prepared and described, wherein $R^1$ is CO or $SO_2$ and $R^2$ is NH or O and where R represents linear or cyclic aliphatic chain and n represents number of linking aliphatic chain carbons (n can be 0, 1, 2 or 3), which are useful in the manufacture of the medicaments due to the carboanhydrase inhibition. These compounds are prepared by nucleophilic reaction of an amine with 4-sulfamoylbenzenesulphonyl chloride in the presence of triethylamine excess in tetrahydrofurane or in ether at temperature 0 to 20° C. The compounds show an antiglaucomatic activity.

16 Claims, No Drawings

SUBSTITUTED SULPHONAMIDES, PROCESS FOR THEIR PREPARATION, PHARMACEUTICAL COMPOSITION COMPRISING THEREOF AND THEIR USE

FIELD OF THE INVENTION

The present invention relates to the substituted sulphonamides, which are useful for use as medicaments.

BACKGROUND OF THE INVENTION

Sulphonamides represent an important group of drugs, the different chemical structures of which show antibacterial, diuretic, cancerostatic properties, they are effective carboanhydrase inhibitors, hypoglycaemics, protease inhibitors and cyclooxygenase inhibitors (C. T. Supuran, A. Casini, A. Scozzafava, Med. Res. Reviews 23 (2003) 535-558.

The subject of the present invention relates to the novel compounds with the valuable properties, appropriate particularly in the manufacture of the pharmaceutical compositions. Proceeding from the fact, that the effective sulphonamide type carboanhydrase inhibitors must have suitable spatial (3D) structure to be able to fill sufficiently active enzyme position on the basis of complementarity (M. Remko, J. Phys. Chem. A 107 (2003) 720-725). In addition to the 3D structure, for the high inhibition activity of the sulphonamides there is a certain balance needed between their water solubility and lipophilicity. These and other physic-chemical properties of sulphonamides fulfilling the conditions of Lipinsky rules are highly effective pharmaceutical agents (M. Remko, C.-W. von der Lieth, Bioorg. Med. Chem. 12 (2004) 5395-5403). On the basis of the studies of the relationship between the structure and the activity of aromatic sulphonamides, there was a group of such compounds developed, which are effective carboanhydrase inhibitors and it shows to be effective as antiglaucomatics. It was established, these compounds decrease effectively intraocular pressure.

SUMMARY OF THE INVENTION

The subject of the present invention relates to the novel, until now unknown substituted sulphonamides having general formula (I)

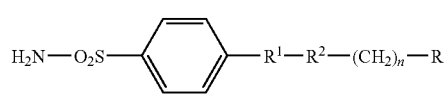
(I)

wherein:
$R^1$ is CO or $SO_2$,
$R^2$ is NH or O,
R includes tertiary $diC_{1-4}$alkylamine group, wherein alkyl moieties are the same or different, or amino group, alkyl moieties of which together form 5, 6 or 7-membered saturated ring, or the ends of the alkyl moieties are linked by heteroatom O, or
R is 4-(N,N-diethylaminoethoxy)benzyl and then $R^1$ is $SO_2$ and $R^2$ is NH; or
R is 4-[N-(morpholinopropyl)sulfamoyl]phenyl and then $R^1$ is CO and $R^2$ is NH.
n is a number of linking aliphatic chain carbons, which is linear or branched, wherein n is 0, 2 or 3.

According to the particular embodiment, the subject of the invention provides the compounds having general formula (I),
wherein:
$R^1$ is $SO_2$ and $R^2$ is NH, and
R and n are shown in the following Table:

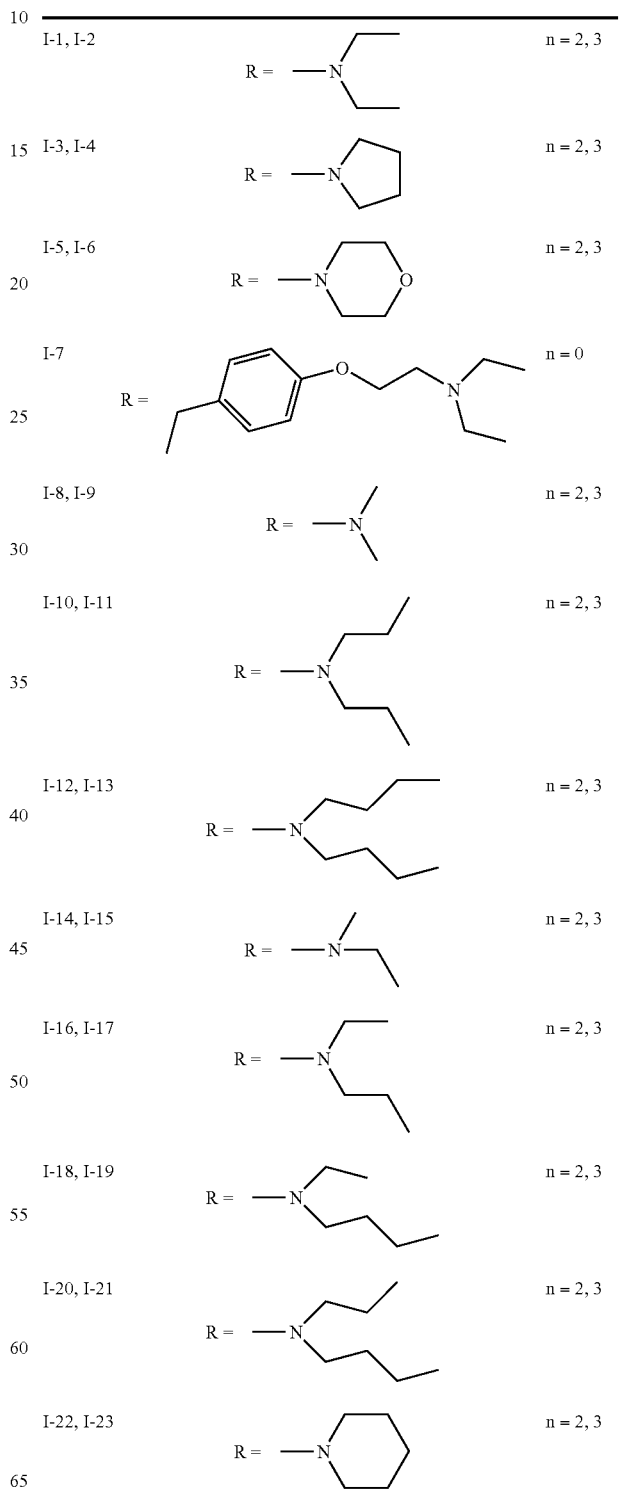

| | | |
|---|---|---|
| I-24, I-25 | 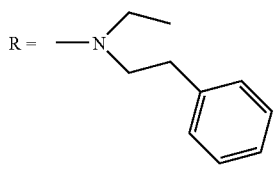 | n = 2, 3 |

| | | |
|---|---|---|
| I-26, I-27 | 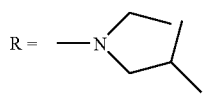 | n = 2, 3 |

According to the further embodiment, the subject of the invention provides the compounds having general formula (I), wherein:
$R^1$ is CO, R, $R^2$ and n are shown in the following Table:

| | | |
|---|---|---|
| II-1, II-2 | 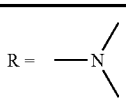 | n = 2, 3  $R^2$ = NH<br>$R^2$ = O |
| II-3, II-4 | 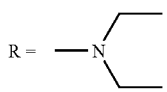 | n = 2, 3  $R^2$ = NH<br>$R^2$ = O |
| II-5, II-6 | 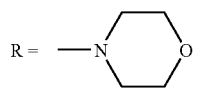 | n = 2, 3  $R^2$ = NH<br>$R^2$ = O |
| II-7 | 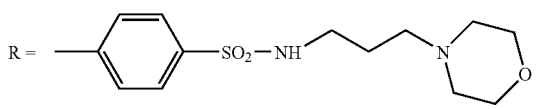 | n = 0  $R^2$ = NH<br>$R^2$ = O |
| II-8, II-9 | 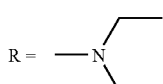 | n = 2, 3  $R^2$ = NH<br>$R^2$ = O |
| II-10, II-11,<br>II-12, II-13 | 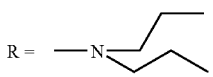 | n = 2, 3  $R^2$ = O<br>$R^2$ = NH |
| II-14, II-15,<br>II-16, II-17 | 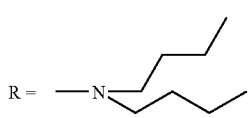 | n = 2, 3  $R^2$ = O<br>$R^2$ = NH |
| II-18, II-19,<br>II-20, II-21 | 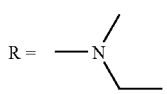 | n = 2, 3  $R^2$ = O<br>$R^2$ = NH |
| II-22, II-23,<br>II-24, II-25 | 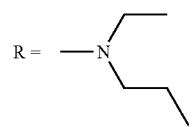 | n = 2, 3  $R^2$ = O<br>$R^2$ = NH |
| II-26, II-27,<br>II-28, II-29 | 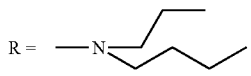 | n = 2, 3  $R^2$ = O<br>$R^2$ = NH |
| II-30, II-31,<br>II-32, II-33 | 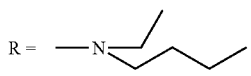 | n = 2, 3  $R^2$ = O<br>$R^2$ = NH |
| II-34, II-35,<br>II-36, II-37 | 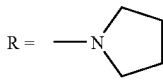 | n = 2, 3  $R^2$ = O<br>$R^2$ = NH |

| | | |
|---|---|---|
| II-38, II-39, II-40, II41 | 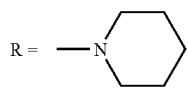 | n = 2, 3   $R^2$ = O $R^2$ = NH |
| II-42, II-43, II-44, II-45 | 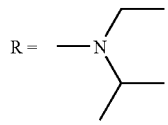 | n = 2, 3   $R^2$ = O $R^2$ = NH |
| II-46, II-47, II-48, II-49 | 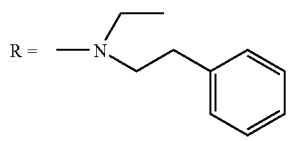 | n = 2, 3   $R^2$ = O $R^2$ = NH |

The subject of the present invention particularly provides these compounds:

N—(N,N-Diethylaminoethyl)benzene-1,4-bis(sulphonamide); (I-1),
N—(N,N-Diethylaminopropyl)benzene-1,4-bis(sulphonamide); (I-2),
N-(Pyrrolidinoethyl)benzene-1,4-bis(sulphonamide); (I-3),
N-(Pyrrolidinopropyl)benzene-1,4-bis(sulphonamide); (I-4),
N-(Morpholinoethyl)benzene-1,4-bis(sulphonamide); (I-5),
N-(Morpholinopropyl)benzene-1,4-bis(sulphonamide); (I-6),
N-(4-Diethylaminoethoxybenzyl)benzene-1,4-bis(sulphonamide); (I-7),
N-(Dimethylaminoethyl)benzene-1,4-bis(sulphonamide); (I-8),
N-(Dimethylaminopropyl)benzene-1,4-bis(sulphonamide); (I-9),
N—(N,N-Dipropylaminoethyl)benzene-1,4-bis(sulphonamide); (I-10),
N—(N,N-Dipropylaminopropyl)benzene-1,4-bis(sulphonamide); (I-11),
N—(N,N-Dibuthylaminoethyl)benzene-1,4-bis(sulphonamide); (I-12),
N—(N,N-Dibuthylaminopropyl)benzene-1,4-bis(sulphonamide); (I-13),
N—(N-Methyl-N-ethylaminoethyl)benzene-1,4-bis(sulphonamide); (I-14),
N—(N-Methyl-N-ethylaminopropyl)benzene-1,4-bis(sulphonamide); (I-15),
N—(N-Ethyl-N-propylaminoethyl)benzene-1,4-bis(sulphonamide); (I-16),
N—(N-Ethyl-N-propylaminopropyl)benzene-1,4-bis(sulphonamide); (I-17),
N—(N-Ethyl-N-buthylaminoethyl)benzene-1,4-bis(sulphonamide); (I-18),
N—(N-Ethyl-N-buthylaminopropyl)benzene-1,4-bis(sulphonamide); (I-19),
N—(N-Propyl-N-buthylaminoethyl)benzene-1,4-bis(sulphonamide); (I-20),
N—(N-Propyl-N-buthylaminopropyl)benzene-1,4-bis(sulphonamide); (I-21),
N-(Piperidinoethy)benzene-1,4-bis(sulphonamide); (I-22),
N-(Piperidinopropyl)benzene-1,4-bis(sulphonamide); (I-23),
N—(N-Ethyl-N-phenylethylaminoethyl)benzene-1,4-bis(sulphonamide); (I-24),
N—(N-Ethyl-N-phenylethylaminopropyl)benzene-1,4-bis(sulphonamide); (I-25),
N—(N-Ethyl-N-isobutylaminoethyl)benzene-1,4-bis(sulphonamide); (I-26),
N—(N-Ethyl-N-isobutylaminopropyl)benzene-1,4-bis(sulphonamide); (I-27),
4-Sulfamoyl-N—(N,N-dimethylaminoethyl)benzamide; (II-1),
4-Sulfamoyl-N—(N,N-dimethylaminopropyl)benzamide; (II-2),
4-Sulfamoyl-N—(N,N-diethylaminoethyl)benzamide; (II-3),
4-Sulfamoyl-N—(N,N-diethylaminopropyl)benzamide; (II-4),
4-Sulfamoyl-N-(morpholinoethyl)benzamide; (II-5),
4-Sulfamoyl-N-(morpholinopropyl)benzamide; (II-6),
4-[N-(Morpholinopropyl)sulfamoyl]phenylsulfamoylbenzamide; (II-7),
(N,N-Diethylaminoethyl)-4-sulfamoylbenzoate; (II-8),
(N,N-Diethylaminopropyl)-4-sulfamoylbenzoate; (II-9),
(N,N-Dipropylaminoethyl)-4-sulfamoylbenzoate; (II-10),
(N,N-Dipropylaminopropyl)-4-sulfamoylbenzoate; (II-11),
4-Sulfamoyl-N—(N,N-dipropylaminoethyl)benzamide; (II-12),
4-Sulfamoyl-N—(N,N-dipropylaminopropyl)benzamide; (II-13),
(N,N-Dibuthylaminoethyl)-4-sulfamoylbenzoate; (II-14),
(N,N-Dibuthylaminopropyl)-4-sulfamoylbenzoate; (II-15),
4-Sulfamoyl-N—(N,N-dibuthylaminoethyl)benzamide; (II-16),
4-Sulfamoyl-N—(N,N-dibuthylaminopropyl)benzamide; (II-17),
(N-Methyl-N-ethylaminoethyl)-4-sulfamoylbenzoate; (II-18),
(N-Methyl-N-ethylaminopropyl)-4-sulfamoylbenzoate; (II-19),
4-Sulfamoyl-N—(N-methyl-N-ethylaminoethyl)benzamide; (II-20),
4-Sulfamoyl-N—(N-methyl-N-ethylaminopropyl)benzamide; (II-21),
(N-Ethyl-N-propylaminoethyl)-4-sulfamoylbenzoate; (II-22),
(N-Ethyl-N-propylaminopropyl)-4-sulfamoylbenzoate; (II-23),
4-Sulfamoyl-N—(N-ethyl-N-propylaminoethyl)benzamide; (II-24),
4-Sulfamoyl-N—(N-ethyl-N-propylaminopropyl)benzamide; (II-25), (N-Propyl-N-buthylaminoethyl)-4-sulfamoylbenzoate; (II-26),
(N-Propyl-N-buthylaminopropyl)-4-sulfamoylbenzoate; (II-27),
4-Sulfamoyl-N—(N-propyl-N-buthylaminoethyl)benzamide; (II-28),
4-sulfamoyl-N—(N-propyl-N-buthylaminopropyl)benzamide; (II-29),
(N-Ethyl-N-buthylaminoethyl)-4-sulfamoylbenzoate; (II-30),
(N-Ethyl-N-buthylaminopropyl)-4-sulfamoylbenzoate; (II-31),
4-Sulfamoyl-N—(N-ethyl-N-buthylaminoethyl)benzamide; (II-32),
4-Sulfamoyl-N—(N-ethyl-N-buthylaminopropyl)benzamide; (II-33),
(Pyrrolidinoethyl)-4-sulfamoylbenzoate; (II-34),
(Pyrrolidinopropyl)-4-sulfamoylbenzoate; (II-35),
4-Sulfamoyl-N-(pyrrolidinoethyl)benzamide; (II-36),
4-Sulfamoyl-N-(pyrrolidinopropyl)benzamide; (II-37),
(Piperidinoethyl)-4-sulfamoylbenzoate; (II-38),
(Piperidinopropyl)-4-sulfamoylbenzoate; (II-39),
4-Sulfamoyl-N-(piperidinoethyl)benzamide; (II-40),
4-Sulfamoyl-N-(piperidinopropyl)benzamide; (II-41),
(N-Ethyl-N-isopropylaminoethyl)-4-sulfamoylbenzoate; (II-42),
(N-Ethyl-N-isopropylaminopropyl)-4-sulfamoylbenzoate; (II-43),
4-Sulfamoyl-N—(N-ethyl-N-isopropylaminoethyl)benzamide; (II-44),
4-Sulfamoyl-N—(N-ethyl-N-isopropylaminopropyl)benzamide; (II-45),
[(N-Ethyl-N-phenylethyl)aminoethyl]-4-sulfamoylbenzoate; (II-46),
[(N-Ethyl-N-phenylethyl)aminopropyl)]-4-sulfamoylbenzoate; (II-47),
4-Sulfamoyl-N—[(N-ethyl-N-phenylethyl)aminoethyl]benzamide; (II-48),
4-Sulfamoyl-N—[(N-ethyl-N-phenylethyl)aminopropyl]benzamide; (II-49), Substituted benzene 1,4-bis(sulphonamides) can be prepared by the nucleophilic reaction of amines (IV) with 4-sulfamoylbenzenesulphonyl chloride (V) in the presence of triethylamine excess in tetrahydrofurane or in ether at the temperature 0 to 20° C. for 12 hours. In the preparation of the compounds (I-1) to (I-4), aliphatic amines IV were used in the reaction, wherein one amino group is primary and the other is tertiary. Carbon linking chain between the nitrogen atoms comprises 2 or 3 carbon atoms. Tertiary amino group contains two alkyl groups, I-1 and I-2, or a nitrogen atom of this tertiary amino group is a part of the ring I-3, I-4, I-5 and I-6. In case of substituted 1,4-bis(sulphonamide) I-7, there was 4-diethylaminoethoxybenzylamine (XI) used as amine.

Substituted 4-sulfamoylbenzamides can be prepared by the nucleophilic reaction of amines having general formula (IV) with 4-sulfamoylbenzoyl chloride (VI) in tetrahydrofurane or in ether in the presence of triethylamine or N,N-diisopropylethylamine excess at the temperature 0 to 20° C. for 12 hours. In the preparation of the compounds II-1 to II-6, there were aliphatic diamines used in the reaction, wherein one amino group is primary and the other is tertiary. Tertiary amino group comprises two alkyl groups or nitrogen atom of this tertiary amino group is a part of the ring. In case of substituted 4-sulfamoylbenzamide (II-7), 4-amino-N-(3-morpholinopropyl)benzene-sulphonamide (XIII) was used as an amine.

For the preparation of the substituted benzoate II-8, 2-diethylaminoethanol was used as a compound with primary amino group.

The scheme for the preparation of the substituted benzene-1,4-bis(sulphonamides)

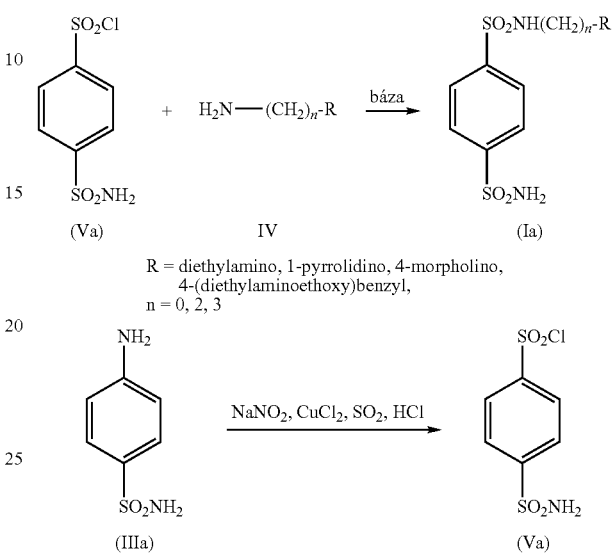

The scheme for the preparation of the substituted benzamides II

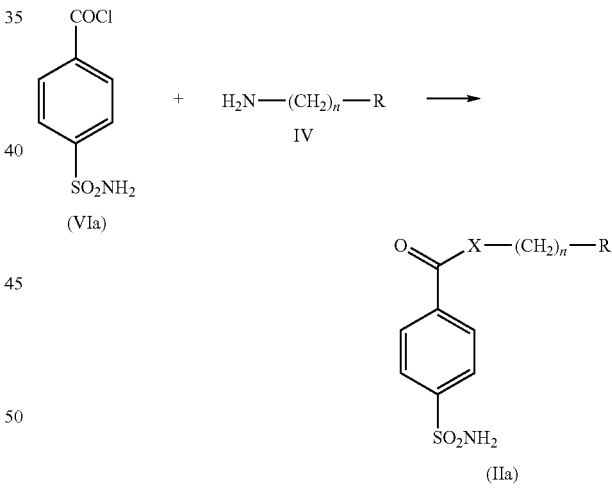

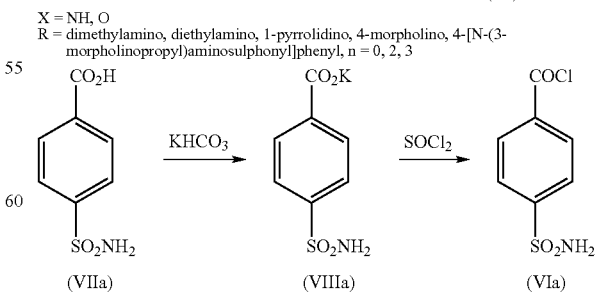

The scheme for the preparation of certain starting compounds set forth in detail in the examples of the embodiment.

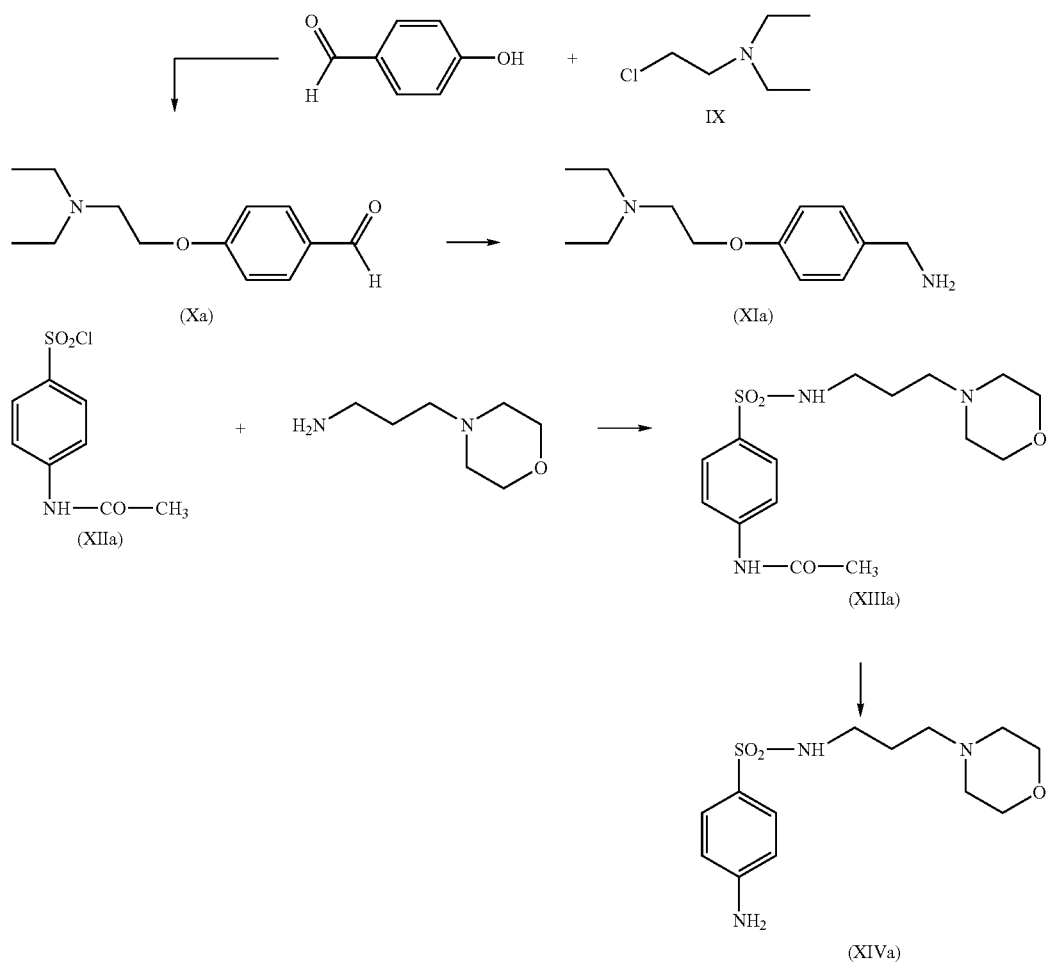

In all cases, the ammonium salts were prepared by the acidobasic reaction of the amino group of the compounds I-7 and II-8 with the solution of hydrogen chloride in methanol.

Compounds of the general formula (I) were tested in the form of their salts with hydrogen chloride. The pH of aqueous solutions of these salts is close to the pH=7 value. $^1$H-NMR were determined on the Mercury Plus 300 MHz spectrometer in the DMSO solution.

The invention also relates to the use of the compounds of the general formula (I) and physiologically and pharmaceutically acceptable salts, hydrates or solvates thereof in the manufacture of the pharmaceutical compositions. For this purpose they can be processed to the appropriate dosage form together with the auxiliaries, alternatively together with one or more other active agents, particularly with the active agents for the treatment of glaucoma.

These compositions according to the present invention can be used as the medicaments in the human and the veterinary medicine. Particular the auxiliaries are selected according to the pharmaceutical formulation and required way of administration.

In the pharmaceutical compositions according to the present invention for the oral, sublingual, subcutaneous, intramuscular, intravenous, topical, intratracheal, intranasal, transdermal, rectal or intraocular administration, the active component of said general formula (I) or the acceptable salts, solvates or hydrates thereof can be administered as unit dosage forms as well as the mixtures with the conventional pharmaceutical vehicles, to the animals and human for the prophylaxis or the treatment of the disorders or diseases associated with carboanhydrase enzyme. Appropriate dosage units include the formulations for oral way administration, such as tablets, gelatine capsules, powders, granules and oral solutions or suspensions, the formulations for sublingual, buccal, intratracheal or intranasal, subcutaneous administration, the formulations for intramuscular or intravenous administration and the formulation for rectal administration. For topical application the compounds of the present invention can be used in creams, ointments, solutions, emulsions, microemulsions, suspensions or in eyewash. If the topical composition is prepared in the form of the solution, specifically in the form of eye drops, main pharmaceutical component is mixed together with auxiliaries, i.e.:

0.001 to 2% by weight, the auxiliaries maintaining the pH conditions (for example: boric acid, sodium borate, sodium phosphate, potassium phosphate and others)

0.001 to 2% by weight, the auxiliaries adjusting isotonicity of the environs (for example: sodium chloride, potassium chloride, glucose, mannitol and others)

0.001 to 2% by weight, the preservatives (for example: benzalconium chloride, chlorohexidine and others)

0.001 to 2% by weight, the auxiliaries adjusting viscosity of the environs (for example: hydroxyethyl cellulose, hydroxymethyl cellulose, povidone, polyvinylalcohol and others)

0.001 to 2% by weight, the antioxidants (for example: citric acid, mannitol, EDTA and other).

These auxiliaries are given as examples, otherwise many other agents can be even used.

Compounds of the general formula (I) and physiologically acceptable salts, hydrates or solvates thereof can be used for prophylaxis and treatment of diseases, particularly for treatment of increased intraocular pressure, glaucoma.

On the basis of the above described assays and below described results of the assays, the synergic effect of our compound together with other antiglaucomatics selected from these groups can be expected: sympathomimetics (clonidine, brimonidine, epinephrine); parasympathomimetics (pilocarpine, carbachole); betablocators (timolol, betaxolol, levobunolol); prostaglandine analogues (latanoprost, bimatoprost, travoprost); and other antiglaucomatics (guanetidine, dapiprazole).

The invention is illustrated by following examples of the present invention embodiment, without limiting it in any way.

EXAMPLES

Preparation of the Starting Compounds

Example 1

Preparation of 4-sulfamoylbenzenesulphonyl chloride (V) [Cross, P. E., Gatsby, B., J. Med. Chem. 21, 845 (1978); Holland, G. F., Funderburk, W. H., J. Med. Chem. 6, 307 (1963)]

To the 700 ml Erlenmeyer flask was taken up 54 ml of the distilled water and 72 ml of the concentrated hydrochloric acid. The solution was cooled to 0° C. and 24 g (0.139 mol) of sulfanilamide III was added successively portionwise under stirring. The mixture was stirred at this temperature another 1 hour. To this mixture, the solution of 9.6 g (0.139 mol) of sodium nitrite in 16 ml of the water was added dropwise for 30 minutes under stirring and cooling, so as the temperature of the mixture does not exceed 0° C. The mixture was then stirred another 30 minutes at the 0° C. In the meantime, the solution of 36 g (0.56 mol) of sulphur dioxide in 120 ml of 99% acetic acid was prepared. Sulphur dioxide was prepared by the successive addition of 100 g of sodium pyrosulphite to 250 ml 40% sulphuric acid. Prepared sulphur dioxide was taken up under cooling to the 120 ml of 99% acetic acid at +5° C. until the weight gain reaches 36 g. To this solution, 1.4 g of copper dichloride dihydrate was added and the mixture was stirred. To this mixture, the solution of prepared diazonium salt it is then added for 5 minutes under gentle stirring for 10 minutes in three portions so as the temperature of the mixture did not exceed +5° C. After about 15 min evolution of forming nitrogen occurs. The mixture was stirred another 15 min, 200 ml of the mixture of the water and the grinded ice was added and the mixture was stirred another 20 min. Obtained solid was separated, washed 3 times with the ice water and dried. Crystallization from ethyl acetate. Colourless solid m.p. 156-157° C. Afforded 14.9 g (42%) of 4-sulfamoylbenzenesulphonyl chloride V.

Example 2

Preparation of sodium 4-sulfamoylbenzoate (VIII) [Gubert, S., Farmaco 45, 59 (1990); Rodionov, V. H., Javorskaja, E. V., Zh. Obsc. Chinn. 18, 110 (1948)]

In the 500 ml Erlenmeyer flask the solution of 20.1 g (0.2 mol) potassium bicarbonate in 180 ml of the distilled water was prepared. To this solution, 40.2 g (0.2 mol) of 4-sulfamoylbenzoic acid VII was added portionwise for 30 minutes under stirring at 45° C., each time until dissolution. The mixture was fizzing by leaking $CO_2$. Then the water was distilled off to the dryness from the solution on the vacuum rotatory evaporator (the temperature of the bath did not exceed 60° C.). Remaining humidity was removed by severalfold azeotropic distillation with toluene on the vacuum evaporator. The solid residue was shaken with dichloromethane, this was decanted and the solid product was dried under the infralamp. Colourless solid. Yield 43 g (98%) of potassium 4-sulfamoylbenzoate VIII.

Example 3

Preparation of 4-sulfamoylbenzoyl chloride (VI) [Gubert, S., Farmaco 45, 59 (1990); Rodionov, V. H., Javorskaja, E. V., Zh. Obsc. Chinn. 18, 110 (1948)]

To the 3-neck flask equipped with the stirrer and the thermometer, fresh distilled 55 ml of thionylchloride was taken up and 3 drops of dimethylformamide was added. The mixture was heated in the oil bath to 40° C. and at this temperature 35.8 g (0.149 mol) of potassium 4-sulfamoylbenzoate VIII was added portionwise for 30 minutes under stirring. Then the mixture was heated to 55° C. for another 40 min. On the vacuum rotatory evaporator, excess thionylchloride was distilled off and the product was extracted 3 times into 100 ml of hot (60° C.) anhydrous dioxane. The solution was diluted with adding 500 ml of petroleum ether. Obtained solid was separated, washed with petroleum ether or hexane and purified by crystallization from chloroform. Almost colourless solid, m.p 151-153° C. Afforded 20 g (61%) of 4-sulfamoylbenzoyl chloride VI.

Example 4

Preparation of 4-diethylaminoethoxybenzaldehyde X [Rodionov, V. H., Javorskaja, E. V., Zh. Obsc. Chim. 18, 110 (1948)]

To the solution of 18.4 g (0.15 mol) of 4-hydroxybenzaldehyde in 100 ml acetone, 27.5 g (0.16 mol) of N,N-diethyl-N-(2-chlorethyl)-amine IX and 22.1 g (0.16 mol) potassium carbonate was added at the room temperature under stirring. The mixture was then intensively stirred at the boiling temperature for 12 hours. The mixture was cooled, potassium chloride was separated, washed with acetone. The solvent was distilled off from the solution on the vacuum rotatory evaporator. Afforded 20 g (60.6%) of 4-diethylaminoethoxybenzaldehyde X. Colourless fluid boiling point 120-123° C./0.5 torr, $n^{20}{}_D$=1.536. Lit. [5] reports boiling point 123-125° C./0.8 torr, $n^{20}{}_D$=1.530.

Example 5

Preparation of 4-diethylaminoethoxybenzylamine XI [Cossey, H. D., Sharpe, C. J., J. Chem. Soc. 4322 (1963). Goldberg, M. W., Moutclair, U., Schw. Pat. 365387 (1962)]

To the solution of 4-diethylaminoethoxybenzaldehyde X in 180 ml 10% solution of ammonia in anhydrous ethanol, 4.5 g RaNi was added and the mixture was heated to 80° C. at the pressure 68 atm in the autoclave under hydrogen input to the reaction mixture under stirring for 12 hours. The mixture was cooled, the catalyst was filtered off, washed with ethanol. The solvent was distilled off from the solution and the distillation residue was purified by distillation under the reduced pressure. Afforded 13 g (65%) of 4-diethylaminoethoxybenzylamine XI. Colourless fluid 138-140° C./0.5 torr, $n^{20}_D$=1.520. Lit. [6.7] reports 130° C./0.3 torr, $n^{20}_D$=1.5220.

Example 6

Preparation of 4-acetamido-N-(3-morpholinopropyl) benzenesulphonamide XIII [Goldberg, M. W., Moutclair, U., U.S. Pat. No. 2,879,293 (1959)]

To the solution of 2.8 g (0.020 mol) of 3-morpholinopropylamine in 15 ml of acetone, the solution of 3.3 g (0.024 mol) of potassium carbonate in 3 ml of water was added under stirring. To this mixture, 5 g (0.021 mol) of 4-acetamidobenzenesulphonyl chloride XII was added portionwise at the room temperature for 15 min. The mixture was then stirred at the room temperature for another 2 hours. One half of the solvent volume was distilled off from the mixture, the mixture was cooled to 0° C., Obtained solid was separated, washed 3 times with 5 ml of ice water and dried. Afforded 4.2 g (62%) of 4-acetamido-N-(3-morpholinopropyl)benzenesulphonamide XIII, colourless solid, m.p. 97-98° C.

Example 7

Preparation of 4-amino-N-(3-morpholinopropyl)benzenesulphonamide XIV [Goldberg, M. W., Moutclair, U., U.S. Pat. No. 2,879,293 (1959)]

The mixture of 3.4 g (0.001 mol) of 4-acetamido-N-(3-morpholinopropyl)benzene sulphonamide XIII and 4 ml of 17% acid was heated for 3.5 hours until slight boiling under stirring. The mixture was cooled to the room temperature and neutralized to chloroform. The solvent was distilled off from the solution and the distillation residue-oil was macerated with ether. Afforded 2.1 g of (71%) 4-amino-N-(3-morpholinopropyl)benzenesulphonamide XIV. Colourless solid, m.p. 96-97° C. Lit. [8] reports 95° C.

Example 8

Preparation of N—(N,N-diethylaminoethyl)benzene-1,4-bis(sulphonamide) (I-1)

To the 250 ml 3 neck flask equipped with the thermometer, the add funnel, the magnetic stirrer, 50 ml of anhydrous tetrahydrofurane (0.0485 mol), N,N-diethylaminoethylamine IV and 24 g of (33 ml) (0.238 mol) triethylamine was taken up. The solution was cooled to 0 to 5° C. and the solution of 12 g (0.0469 mol) of 4-sulfamoylbenzenesulphonyl chloride V in 50 ml anhydrous tetrahydrofurane or ether was for 30 min added under cooling and stirring at 0 to 15° C. The solid was separated. The mixture was then stirred for 12 hours at the room temperature. 100 ml of petroleum ether was added to the solution, the mixture was stirred, the semi-solid product was filtered off. This was triturated with 15 ml of saturated aqueous solution of sodium chloride. The solid product was separated, washed 2 times with 10 ml ice water and dried. Purification with crystallization from the water:ethanol mixture (2:1). Afforded 7.4 g (47%) of N—(N,N-diethylaminoethyl)benzene-1,4-bis(sulphonamide) I-1. Colourless solid, m.p. 128-130° C. Ammonium salt was prepared by acidification at pH=4 of 5 g (0.015 mol) of this base solution in 50 ml of methanol with 10 to 20% hydrogen chloride solution in methanol. 50 ml ether was added to the mixture. Obtained solid was filtered off, washed with ether and purified with crystallization from the water:ethanol mixture (3:1). Afforded 4.6 g (82%) of ammonium salt of the agent I-1. Colourless solid matter, m.p. 185 to 187° C.

H-NMR of the compound I-1. HCl

I-1 (salt) δ $CH_3$ 1.166, 1.177, 1.190, t (6H), $CH_2$ 3.992, 3.112, 3.123, m (6H) $CH_2$ 3.163, 3.169, 3.172 m (2H) $SO_2$—$NH_2$ 7.653, s (H) Har. 8.036, (4H) $SO_2$—NH 8.383, 8.395, 8.405, t (1H) $NH^+$ 10.173, s (1H).

Instead of tetrahydrofurane, ether can be used (5.6 g) and instead of triethylamine, N,N'-diisopropylethylamine (DIPEA) can be used.

Example 9

Preparation of N—(N,N-diethylaminopropyl)benzene-1,4-bis(sulphonamide) (I-2)

The procedure as in Example 8 (compound I-1). 6.3 g (0.0485 mol) N,N-Diethylamino-propylamine was used. Afforded 7.4 g (47%) of N—(N,N-diethylaminopropyl)benzene-1,4-bis(sulphonamide). Colourless solid, m.p. 133-135° C. For the preparation of the ammonium salt 5.3 g (0.015 mol) of the base I-2 was used. Afforded 5.0 g (90.3%) of the ammonium salt of compound I-2. Colourless solid, m.p. 198-200° C.

H-NMR:

I-2 (salt) δ $CH_3$ 1.156, 1.180, 1.205, t (6H) $CH_2$ 1.780-1.800 m (2H) $CH_2$ 2.864-2.884 m (2 (2H) $CH_2$ 2.997, –3.053 m (6H) $SO_2$—$NH_2$ 1.648, s (2H) Har 7.982, 8.011, 8.027, 8.057 dd (4H) $SO_2$—NH 8.068, 8.090, 8.094 t (1H) $NH^+$ 10.254, s (1H).

Example 10

Preparation of N-(pyrrolidinopropyl)benzene-1,4-bis(sulphonamide) (I-4)

The procedure as is Example 8. 6.2 g (0.0485 mol) of Pyrrolidinopropylamine was used. Afforded 6.7 g (41.0%) of N-(pyrrolidinopropyl)benzene-1,4-bis(sulphonamide). Colourless solid, m.p. 120-122° C. For the preparation of the ammonium salt 5.5 g (0.0158 mol) of the base I-4 was used. According to the procedure as in Example 8, 5.2 g (85.8%) of the ammonium salt of compound I-4 was afforded. Colourless solid, m.p. 180-183° C.

H-NMR:

I-4 (salt) δ $CH_2$ 1.835, 1.852, 1.875, 1.904, 1.943, 1.969 m (6H) $CH_2$ 2.856-2.898 m (4H) $CH_2$ 3.044-3.113 m (2H) Har 7.987, 8.015, 8.026, 8.054 dd (4H) $SO_2$—NH 8.079, 8.098, 8.118 t (1H) $NH^+$ 10.868 s (1H).

Example 11

Preparation of N-(morpholinopropyl)benzene-1,4-bis(sulphonamide) (I-6)

The procedure as is Example 8.7 g (0.0485 mol) of Morpholinopropylamine was used. Afforded 8.2 g (48.0%) of N-(morpholinopropyl)-1,4-bis(sulphonamide) I-6. Colourless solid, m.p. 121-123° C.

H-NMR:

I-6 (base) δ $CH_2$-middle 1.533, 1.564, 1.574 t (3H) $CH_2$ 2.377, m (4H) $CH_2$—N 2.806, 2.818, 2.829 t (2H) $CH_2$ 3.557 m (6H) SO$_2$—NH$_2$ 7.607 s (2H) SO$_2$—NH 7.865, s (1H) Har 7.962, 7.975, 8.010, 8.023 dd (4H).

For the preparation of the ammonium salt 6.0 g (0.0173 mol) of the base I-6 was used. The procedure as is Example 8. Afforded 4.9 g (86.0%) of ammonium salt of compound I-6. Colourless solid, m.p. 232-234° C.

H-NMR:

I-6 (salt) δ CH$_2$ 1.813-1.912 m (2H) CH$_2$ 2.823-2.881 m (2H) CH$_2$ 2.953-3.102 m (4H) CH$_2$ 3.322-3.363 m (2H) CH$_2$ 3.731-3.964 m (4H) SO$_2$—NH$_2$ 7.642 s (2H) Har 8.002, 8.011, 8.022, 8.032 dd (4H) SO$_2$—NH 8.053, 8.076, 8.096 t (1H) NH$^+$ 10.893 s (1H).

Example 12

Preparation of N-(4-diethylaminoethoxybenzypenzene-1,4-bis(sulphonamide) (I-7)

The procedure as in Example 8. 10.8 g (0.0485 mol) of 4-Diethylaminoethoxybenzylamine XI was used. Afforded 8.6 g (37.7%) of N-(4-diethylaminoethoxybenzyl)benzene-1,4-bis(sulphonamide) I-7. Colourless solid, m.p. 72-74° C.

For the preparation of the ammonium salt, the procedure as in Example 8 was used. For the preparation of the ammonium salt, 7.8 g (0.0176 mol) of the base I-7 was used. Afforded 6.4 g (76.2%) of the ammonium salt of compound I-7. Colourless solid, m.p. 92-94° C.

H-NMR:

I-7 (salt) δ CH$_3$ 1.217, 1.242, 1.265 t (6H) CH$_2$ 3.166-3.217 m (4H) CH$_2$—N 3.960, 3.981 d (2H) CH$_2$—O 4.315, 4.318, 4.321 t (2H) Har (O-phenyl) 6.87, 380, 7, 6.906, 7.159, 7.188 dd (4H) SO$_2$—NH$_2$ 7.635 s (2H) Har (S-phenyl) 7.961-7.971 dd (4H) SO$_2$—NH 8.380, 8.384, 8.387 t (1H) NH$^+$ 10.230 s (1H).

Example 13

Preparation of 4-sulfamoyl-N—(N,N-dimethylaminoethyl)benzamide (II-1)

To the 250 ml 3 neck flask equipped with the thermometer, the add funnel and the stirrer, 40 ml of tetrahydrofurane or ether, 4.3 g (0.0485 mol) of N,N-dimethylaminoethylamine and 24 g (33 ml) (0.238 mol) of triethylamine or DIPEA (diisopropylethylamine) was taken up. The solution was cooled to 0° C. and the solution of 10.3 g (0.0470 mol) of sulfamoylbenzoyl chloride IX in 60 ml tetrahydrofurane or ether was added dropwise for 30 min under cooling and stirring so as the temperature did not exceed 0 to 15° C. The mixture was then stirred for 12 hours the at room temperature. 100 ml of petroleum ether or hexane was added to the mixture. The semi-solid product was filtered off and macerated with 20 ml of ice-cooled saturated aqueous sodium chloride solution. The solid product was separated, washed once with 10 ml saturated aqueous sodium chloride solution, 2 times with ice water and purified with crystallization from the water:ethanol (2:1). Afforded 6.1 g (48.0%) of 4-sulfamoyl-N-(2-dimethylaminoethyl)benzamide 1'-1. Colourless solid, m.p. 150-151° C.

H-NMR:

II-1 (base) δ CH$_3$ 2.182 t (6H) CH$_2$—N+2.389, 2.412, 2.435 t (2H) CH$_2$—NCO 3.356-3.376 m (2H) SO$_2$—NH$_2$ 7.472 s (2H) SO$_2$—NH$_2$ 7.472 s (2H) Har 7.871, 7.899, 7.962, 7.991 dd (4H), CO—NH 8.590, 8.594, 8.958 t (1H).

Ammonium salt was prepared by acidification to pH=5 of 5 g (0.015 mol) of this compound II-1 solution in 40 ml of methanol with 10 to 20% hydrogen chloride solution in methanol. 80 ml of ether was added to the mixture, the solid was filtered off and purified with crystallization from water:ethanol (1:2). Afforded 4.5 g (80.4%) of ammonium salt of compound II-1. Colourless solid, m.p. 208-210° C.

H-NMR:

II-1 (salt) δ CH$_3$ 2.821 s (6H) CH$_2$—N+3.270, 3.270, 3.278, 3.297 t (2H) CH$_2$—NCO 3.630, 3.649, 3.668 t (2H) SO$_2$—NH$_2$ 7.524 s (2H) Har 7.896, 7.924, 8.084, 8.113 dd (4H) CO—NH 9.087, 9.104, 9.123 t (1H) NH$^+$ 10.365 s (1H).

Example 14

Preparation of 4-sulfamoyl-N—(N,N-diethylaminoethyl)benzamide (II-3)

The procedure as in Example 13. 5.6 g (0.0485 mol) of N,N-diethylaminoethylamine was used. Afforded 6.2 g (44.0%) of 4-sulfamoyl-N-(2-diethylaminoethyl)benzamide. Colourless solid, m.p. 174-176° C.

H-NMR:

II-3 (base) δ CH$_3$ 0.945, 0.969, 0.993 t (6H) CH$_2$ 2.501-2.584 m (8H) SO$_2$—NH$_2$ 7.466 s (2H) Har 7.873, 7.900, 7.957, 7.985 dd (4H) CO—NH 8.568, 8.571, 8.574 t (1H).

For the preparation of the ammonium salt 5.2 g (0.0184 mol) of base II-3 was used. According to the procedure as in Example 13, 5.1 g (85.4%) of the ammonium salt of compound II-3 was used. Colourless solid, m.p. 201-202° C.

H-NMR:

II-3 (salt) δ CH$_3$ 1.203, 1.233, 1.254 t (6H) CH$_2$ 3.161-3.203 m (6H) CH$_2$—N+3.66 m (2H) SO$_2$—NH$_2$ 7.51 s (2H) Har 7.903, 7.932, 8.084, 8.101 dd (4H) CO—NH 9.142, 9.173, 9.212 t (1H) NH$^+$ 10.383 s (1H).

Example 15

Preparation of 4-sulfamoyl-N—(N,N-diethylaminopropyl)benzamide (II-4)

The procedure as in Example 13. 6.2 g (0.0485 mol) of N,N-diethylaminopropylamine was used. Afforded 6.2 g (44.0%) of 4-sulfamoyl-N—(N,N-diethylaminopropyl)benzamide II-4. Colourless solid, m.p. 122-123° C. For the preparation of the ammonium salt, 5.2 g (0.0184 mol) of base was used. According to the procedure as in Example 13, 5.2 g (85.4%) of the ammonium salt of compound II-4. was afforded. Colourless solid, m.p. 165-167° C.

H-NMR:

II-4 (salt) δ CH$_3$ 1.173, 1.197, 1.221 t (6H) CH$_2$ middle 1.900-1.958 m (2H) CH$_2$ (3.350-3.358) m (2H) SO$_2$—NH$_2$ 7.513 s (2H) Har 7.887, 7.914, 8.018, 8.045 dd (4H) CO—NH 8.936, 8.940, 8.944 t (1H) NH$^+$ 10.250 s (1H).

Example 16

Preparation 4-sulfamoyl-N-(morpholinopropyl)benzamide (II-6)

The procedure as in Example 13. 7.0 g (0.0485 mol) of morpholinopropylamine was used and 7.3 g (47.7%) of 4-sulfamoyl-N-(morpholinopropyl)benzamide II-6 was afforded. Colourless solid, m.p. 196-198° C.

H-NMR:

II-6 (base) δ CH$_2$ (middle)) 1.643, 1.666, 1.689, 1.712, 1.736 quintet (2H) CH$_2$ 2.306-2.353 m (6H) CH$_2$ 3.272-3.294 m (2H) (CH$_2$)$_2$O 3.548, 3.564, 3.580 t (4H) SO$_2$—NH$_2$ 7.477 s (2H) Har 7.874, 7.880, 7.897, 7.903, 7.971, 7.987, 7.994 m (4H) CO—NH 8.644, 8.662, 8.680 t (1H).

For the preparation of the ammonium salt, 6.0 g (0.0183 mol) of base II-6 was used. According to the procedure as in Example 13, 5.9 g (88.0%) of the ammonium salt of compound II-6 was used. Colourless solid, m.p. 196-198° C.

H-NMR:

II-6 (salt) δ $CH_2$ 1.963-2.040 m (2H) $CH_2$ 2.991-3.152 m (4H) $SO_2$—$NH_2$ 7.510 s (2H) Har 7.892, 7.923, 8.021 8.053 dd (4H) CO—NH 8.912, 8.933, 8.952 t (1H) $NH^+$ 10.992 s (1H).

Example 17

Preparation of 4-[N-(morpholinopropyl)sulfamoyl] phenylsulfamoylbenzamide; (II-7)

The procedure as in Example 13. 14.6 g (0.0485 mol) of 4-Amino-N-(morpholinopropyl)-benzene-sulphonamide XIII was used and 10.1 g (44.5%) of 4-sulfamoyl-N-[4-(morpholinopropyl)aminosulphonylphenyl]benzamide II-7 was afforded. Pale yellow oil.

H-NMR:

II-7 (base) δ $CH_2$ 1.493, 1.522, 1.543 t (2H) $CH_2$ 3.510-3.542 m (6H) $SO_2$—NH 7.502, 7.523, 7.541 t (1H) $SO_2$—NH2 7.562 s (1H) Har (CO-phenyl) 7.776, 1.805, 8.109, 8.137 dd (4H) Har (N-phenyl) 7.961, 7.973, 7.990, 8.003 dd (4H) CO—NH 10.763 s (1H).

For the preparation of the ammonium salt, 8.0 g (0.0166 mol) of base II-7 was used. According to the procedure as in Example 13, 7.0 g (81.4%) of the ammonium salt of compound II-7 was afforded. Colourless solid, m.p. 201-202° C.

H-NMR:

II-7 (salt) $CH_2$ (middle) 1.815, 1.840, 1.865 t (2H) $CH_2$ 2.780, 2.802, 2.823, 2.844 m (2H) $CH_2$ 3.921, 3.960 d (2H) $SO_2$—NH2 7.500 s (2H), $SO_2$—NH 7.706, 7.746 t (1H) Har (CO-phenyl) 7.796, 7.825, 8.126, 8.154 dd (4H) Har (N-phenyl) 7.962, 7.990, 8.005, 8.035 dd (4H) $NH^+$ 10.568 s (1H) CO—NH 10.842 s (1H).

Example 18

Preparation of N,N-diethylaminoethyl-(4-sulfamoylbenzoate) II-8

The procedure as in Example 13. 5.7 g (0.0485 mol) of N,N-diethylaminoethanol was used. Afforded 6.1 g (43.3%) of N,N-diethylaminoethyl-(4-sulfamoylbenzoate) II-8. Colourless solid, m.p. 159-160° C. For the preparation of the ammonium salt, 5.1 g (0.017 mol) of base II-8 was used. According to the procedure as in Example 13, 4.4 g (77.2%) of the ammonium salt of compound II-8 was afforded. Colourless solid, m.p. 185-186° C.

H-NMR:

II-8 (salt) δ $CH_3$ 1.242, 1.273, 1.291 t (3H) $CH_2$ 3.203-3.242 m (4H) $CH_2$ 3.522-3.541 m (2H) $CH_2$ 4.653-4.702 m (2H) $SO_2$—$NH_2$ 7.621 s (1H) Har 7.962, 7.993, 8.210, 8.243 dd (4H) $NH^+$ 10.633 s (1H).

Example 19

The Results of Effectiveness Assays

Effectiveness of the compounds according to of the invention is supported with the results of the pharmacological assays.

The basic pharmacologic profile of the compounds of the general formula (I), which was focused on the determination of the intraocular pressure changes, was evaluated in in vivo conditions. In addition to the main potential therapeutic effect, related side responses were also monitored. In the experiments the laboratory animals of chinchilla species were used, because the normotension eye of this animal species provides the best reactivity. Adult male Chinchilla (in the age of one to one and half year), of 2000-3500 g, examined by veterinarian, without disease symptoms, grown under the standard conditions was used as the animal model. The solutions of tested compounds of the general formula (I) were always freshly prepared. The distilled water was used as a control. Measurement apparatus Tono-Pen®XL from Medtronic XOMED was used for measurement of the intraocular pressure. The intraocular pressure values were expressed in mmHg. At the first day of the experiment the solutions of the tested compounds of the general formula (I) were applied twice a day, specifically at 8.00 a.m. and 2.00 p.m. At the second day of the experiment the application was still in the $30^{th}$ hour (i.e. at the second day at 2.00 p.m.).

The solution of each compound was always applied in an amount of 2 drops into the right conjunctiva sac. The left eye served as a control. Into the conjunctiva sac of this eye (left), the same number of drop (2 drops) of distilled water was applied. The distilled water served as placebo.

Into the conjunctiva sac of both eyes one drop of the local anesthetic (oxybuprocain) was administered and massaged by careful circular movement (1-2), before the measurement of the intraocular activity both of the compound solution or the distilled water.

Standard requirements were kept in all measurements. The measurements started in the morning at 7.00 a.m. The measurement was accomplished with Tono-Pen® XL apparatus by soft perpendicular touch of the probe to the cornea of the rabbit five times successively. The measurement was accomplished on the both cornea (right and left eyes) before administration of the sample. Thus the normal values of the intraocular pressure for both the right and left eyes were obtained. Then at 8.00 a.m. 2 drops of tested compound were applied in the right eye and 2 drops of the distilled water were applied in the left eye.

Further measurements were carried out after half an hour (at 8.30 a.m.), after one hour (at 9.00 a.m.), after four hours (at 12.00), after seven hours (at 3.00 p.m.), after 25 hours (on the second day at 9.00 a.m.) and after 31 hours from the application in the right eye (on the second day at 3.00 p.m). The intraocular pressure changes in the left eye of the rabbit after placebo application, i.e. 2 drops of distilled water, were monitored in the same time intervals. Moreover, 2 drops of the tested compound in the right eye and 2 drops of distilled water in the left eye were applied again in the same group of the rabbits in the first day at 2.00 p.m. (i.e. 6 hours after application of the first dose of the compound) and in the second day of the experiment at 2.00 p.m. (i.e. in the $30^{th}$ hour of the experiment). Thus the changes caused by the repeated administration of the compound can be monitored. For each compound and each concentration 10 independent assays were carried out.

No negative side effects were observed during the experiments.

Tables show a the absolute number values obtained by monitoring of compound 1-6 at the concentration of 2% and 2.5% and of compound 11-6 at the concentration of 1% in determined time intervals.

| | Measured intraocular pressure values [mmHg] | | | | | | | | | | | | | |
|---|---|---|---|---|---|---|---|---|---|---|---|---|---|---|
| | N | | 0.5 h | | 1 h | | 4 h | | 7 h | | 25 h | | 31 h | |
| n | LE | RE | LE | RE | LE | RE | LE | RE | LE | RE | LE | RE | LE | RE |
| 1 | 14 | 14 | 11 | 11 | 16 | 14 | 11 | 7 | 7 | 5 | 11 | 12 | 11 | 11 |
| 2 | 14 | 15 | 9 | 9 | 9 | 11 | 7 | 7 | 6 | 5 | 9 | 9 | 9 | 8 |
| 3 | 12 | 13 | 13 | 12 | 10 | 10 | 8 | 8 | 7 | 6 | 11 | 12 | 9 | 10 |
| 4 | 16 | 14 | 13 | 15 | 15 | 13 | 7 | 12 | 6 | 7 | 13 | 12 | 14 | 14 |
| 5 | 12 | 14 | 12 | 9 | 9 | 12 | 8 | 7 | 7 | 6 | 13 | 15 | 14 | 9 |
| 6 | 10 | 11 | 6 | 7 | 12 | 8 | 9 | 8 | 7 | 10 | 9 | 8 | 12 | 9 |
| 7 | 10 | 12 | 9 | 7 | 9 | 9 | 8 | 6 | 8 | 8 | 11 | 9 | 13 | 10 |
| 8 | 12 | 13 | 8 | 8 | 10 | 9 | 8 | 8 | 7 | 8 | 8 | 9 | 9 | 9 |
| 9 | 10 | 13 | 8 | 9 | 10 | 9 | 10 | 9 | 9 | 8 | 10 | 9 | 12 | 11 |
| 10 | 10 | 10 | 9 | 9 | 9 | 8 | 9 | 12 | 10 | 10 | 9 | 12 | 13 | 13 |
| Average | 12 | 12.9 | 9.8 | 9.6 | 10.9 | 10.3 | 8.5 | 8.4 | 7.4 | 7.3 | 10.4 | 10.7 | 11.6 | 10.4 |
| SD | 2.11 | 1.52 | 2.35 | 2.46 | 2.60 | 2.11 | 1.27 | 2.07 | 1.26 | 1.83 | 1.71 | 2.21 | 2.01 | 1.90 |
| SE ± | 0.67 | 0.48 | 0.74 | 0.78 | 0.82 | 0.67 | 0.40 | 0.65 | 0.40 | 0.58 | 0.54 | 0.70 | 0.64 | 0.60 |
| p (t-test) versus N | | | 0.003 | 0.001 | 0.069 | 0.000 | 0.002 | 0.000 | 0.001 | 0.000 | 0.018 | 0.009 | 0.345 | 0.009 |
| P (t-test) L vs R | | 0.144 | | 0.427 | | 0.289 | | 0.449 | | 0.444 | | 0.369 | | 0.093 |

Compound I-6, concentration of 2%
N—normal value before application
SD—standard deviation
SE—standard error of the average
LE—left eye
RE—right eye

| | Measured intraocular pressure values [mmHg] | | | | | | | | | | | | | |
|---|---|---|---|---|---|---|---|---|---|---|---|---|---|---|
| | N | | 0.5 h | | 1 h | | 4 h | | 7 h | | 25 h | | 31 h | |
| n | LE | RE | LE | RE | LE | RE | LE | RE | LE | RE | LE | RE | LE | RE |
| 1 | 15 | 14 | 10 | 9 | 9 | 10 | 13 | 11 | 8 | 8 | 12 | 15 | 8 | 9 |
| 2 | 14 | 15 | 10 | 12 | 12 | 9 | 12 | 10 | 10 | 10 | 13 | 13 | 10 | 16 |
| 3 | 12 | 12 | 12 | 9 | 18 | 13 | 12 | 13 | 15 | 11 | 13 | 14 | 12 | 13 |
| 4 | 13 | 14 | 16 | 16 | 13 | 16 | 12 | 11 | 14 | 16 | 13 | 13 | 16 | 15 |
| 5 | 13 | 16 | 12 | 11 | 8 | 11 | 12 | 9 | 10 | 9 | 13 | 15 | 12 | 12 |
| 6 | 14 | 16 | 10 | 10 | 9 | 9 | 10 | 10 | 6 | 7 | 12 | 11 | 9 | 9 |
| 7 | 18 | 17 | 9 | 11 | 11 | 10 | 8 | 8 | 7 | 9 | 10 | 12 | 10 | 9 |
| 8 | 18 | 18 | 10 | 10 | 10 | 9 | 9 | 9 | 8 | 9 | 13 | 12 | 13 | 10 |
| 9 | 16 | 15 | 12 | 12 | 9 | 9 | 9 | 9 | 8 | 8 | 13 | 12 | 9 | 9 |
| 10 | 18 | 16 | 10 | 10 | 11 | 9 | 13 | 11 | 11 | 9 | 13 | 13 | 12 | 10 |
| Average | 15.1 | 15.3 | 11.1 | 11 | 11 | 10.5 | 11 | 10.1 | 9.7 | 9.6 | 12.5 | 13 | 11.1 | 11.2 |
| SD | 2.28 | 1.70 | 2.02 | 2.05 | 2.91 | 2.32 | 1.83 | 1.45 | 2.95 | 2.50 | 0.97 | 1.33 | 2.38 | 2.66 |
| SE ± | 0.72 | 0.54 | 0.64 | 0.65 | 0.92 | 0.73 | 0.58 | 0.46 | 0.93 | 0.79 | 0.31 | 0.42 | 0.75 | 0.84 |
| p(t-test) vs N | | | 0.005 | 0.000 | 0.008 | 0.001 | 0.003 | 0.000 | 0.002 | 0.000 | 0.008 | 0.011 | 0.003 | 0.003 |
| p(t-test) L vs R | | 0.413 | | 0.457 | | 0.338 | | 0.119 | | 0.468 | | 0.175 | | 0.465 |

Compound I-6, concentration of 2.5%
N—normal value before application
SD—standard deviation
SE—standard error of the average
LE—left eye
RE—right eye

| | Measured intraocular pressure values [mmHg] | | | | | | | | | | | | | |
|---|---|---|---|---|---|---|---|---|---|---|---|---|---|---|
| | N | | 0.5 h | | 1 h | | 4 h | | 7 h | | 25 h | | 31 h | |
| n | L'O | PO | L'O | PO | L'O | PO | L'O | PO | L'O | PO | L'O | PO | L'O | PO |
| 1 | 14 | 14 | 11 | 10 | 12 | 14 | 8 | 8 | 7 | 6 | 13 | 12 | 11 | 10 |
| 2 | 18 | 14 | 12 | 9 | 11 | 9 | 8 | 8 | 8 | 8 | 13 | 12 | 12 | 9 |
| 3 | 13 | 10 | 12 | 10 | 12 | 8 | 8 | 6 | 7 | 6 | 14 | 12 | 11 | 11 |
| 4 | 18 | 17 | 18 | 14 | 13 | 12 | 12 | 11 | 13 | 13 | 14 | 16 | 11 | 14 |
| 5 | 17 | 18 | 15 | 14 | 15 | 12 | 12 | 13 | 11 | 12 | 12 | 13 | 14 | 14 |
| 6 | 11 | 11 | 10 | 9 | 11 | 12 | 10 | 8 | 9 | 9 | 11 | 12 | 10 | 9 |
| 7 | 16 | 15 | 11 | 8 | 11 | 7 | 10 | 12 | 8 | 8 | 11 | 13 | 10 | 10 |
| 8 | 15 | 16 | 13 | 11 | 13 | 10 | 11 | 10 | 9 | 9 | 16 | 16 | 12 | 12 |
| 9 | 15 | 17 | 12 | 11 | 13 | 10 | 11 | 9 | 10 | 9 | 16 | 18 | 10 | 10 |
| 10 | 18 | 26 | 12 | 10 | 12 | 10 | 11 | 11 | 11 | 11 | 15 | 13 | 12 | 12 |

-continued

| | Measured intraocular pressure values [mmHg] | | | | | | | | | | | | | |
|---|---|---|---|---|---|---|---|---|---|---|---|---|---|---|
| | N | | 0.5 h | | 1 h | | 4 h | | 7 h | | 25 h | | 31 h | |
| n | L'O | PO | L'O | PO | L'O | PO | L'O | PO | L'O | PO | L'O | PO | L'O | PO |
| Average | 15.5 | 15.8 | 12.6 | 10.6 | 12.3 | 10.4 | 10.1 | 9.6 | 9.3 | 9.1 | 13.5 | 13.7 | 11.3 | 11.1 |
| SD | 2.37 | 4.42 | 2.32 | 2.01 | 1.25 | 2.12 | 1.60 | 2.17 | 1.95 | 2.33 | 1.84 | 2.16 | 1.25 | 1.85 |
| SE ± | 0.75 | 1.40 | 0.73 | 0.64 | 0.40 | 0.67 | 0.50 | 0.69 | 0.62 | 0.74 | 0.58 | 0.68 | 0.40 | 0.59 |
| p (t-test) versus N | | | 0.001 | 0.002 | 0.001 | 0.003 | 0.000 | 0.000 | 0.000 | 0.000 | 0.021 | 0.080 | 0.000 | 0.002 |
| p (t-test) L vs R | | 0.426 | | 0.027 | | 0.013 | | 0.282 | | 0.419 | | 0.413 | | 0.390 |

Compound II-6, concentration of 1%
N—normal value before application
SD—standard deviation
SE—standard error of the average
LE—left eye
RE—right eye Industrial Utilization Substituted sulphonamides of the general formula I are useful as active compounds in the manufacture of the pharmaceutical compositions, drugs, in human and veterinary medicine, particularly as antiglaucomatics. They are effective carboanhydrase inhibitors and therefore they can have a wide use in the treatment of all diseases, where it is necessary to inhibit this enzyme.

The invention claimed is:

1. A method for the treatment of a patient for glaucoma comprising administering to said patient an effective amount of a substituted sulphonamide selected from the group consisting of
(A) a sulphonanide having the general formula (I)

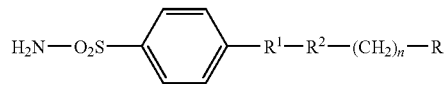

wherein:
$R^1$ is selected from the group consisting of CO and $SO_2$,
$R^2$ is selected from the group consisting of NH and O,
R is a tertiary $diC_{1-4}$alkylamino group, wherein alkyl moieties are the same or different, or an amino group, alkyl moieties of which form together 5, 6 and 7-membered saturated ring, or their ends are linked by heteroatom O, with the proviso that R is 4-(N,N-diethylaminoethoxy)benzyl when $R^1$ is $SO_2$ and $R^2$ is NH; and R is 4-[N-(morpholinopropyl)sulfamoyl]phenyl when $R^1$ is CO and $R^2$ is NH, n is a number of carbons of linking aliphatic chain, which is linear or branched, wherein n is 0, 2 or 3, and (B) physiologically acceptable salts, hydrates or solvates thereof.

2. The method according to claim 1, wherein when $R^1$ is CO, $R^2$, R and n are shown in the following Table:

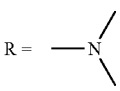

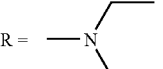

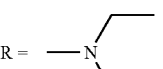

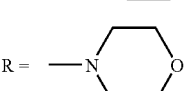

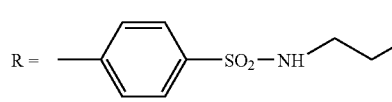

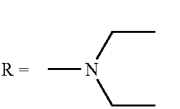

-continued

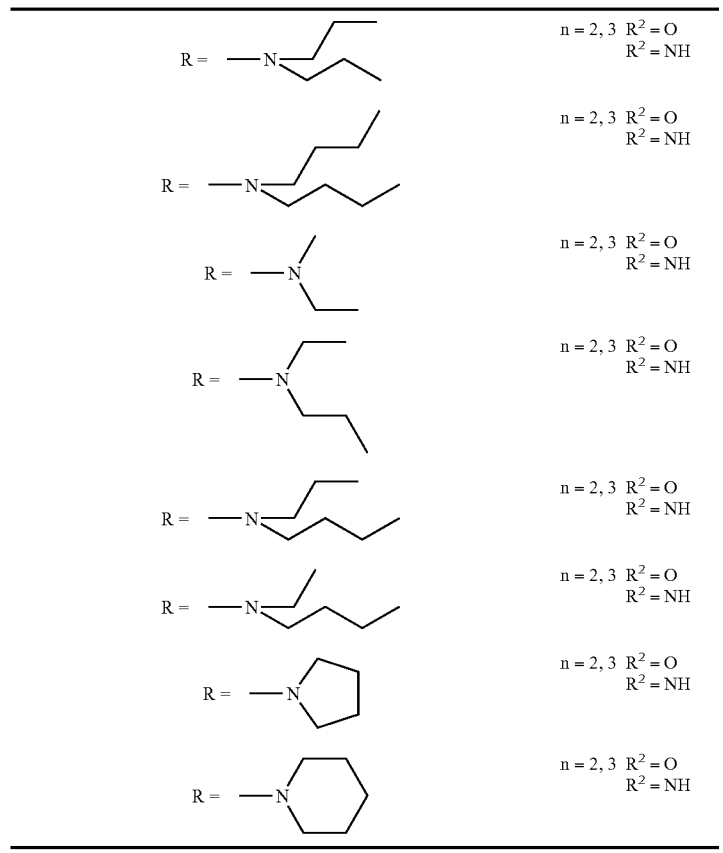

| | |
|---|---|
| R= —N(propyl)(propyl) | n = 2, 3 R² = O<br>R² = NH |
| R= —N(butyl)(butyl) | n = 2, 3 R² = O<br>R² = NH |
| R= —N(methyl)(ethyl) | n = 2, 3 R² = O<br>R² = NH |
| R= —N(ethyl)(propyl) | n = 2, 3 R² = O<br>R² = NH |
| R= —N(ethyl)(butyl) | n = 2, 3 R² = O<br>R² = NH |
| R= —N(methyl)(propyl) | n = 2, 3 R² = O<br>R² = NH |
| R= —N(pyrrolidine) | n = 2, 3 R² = O<br>R² = NH |
| R= —N(piperidine) | n = 2, 3 R² = O<br>R² = NH | and physiologically acceptable salts, hydrates or solvates thereof.

3. The method according to claim 1, wherein
R¹ is SO₂,
R² is NH, and
R and n are shown in the following Table:

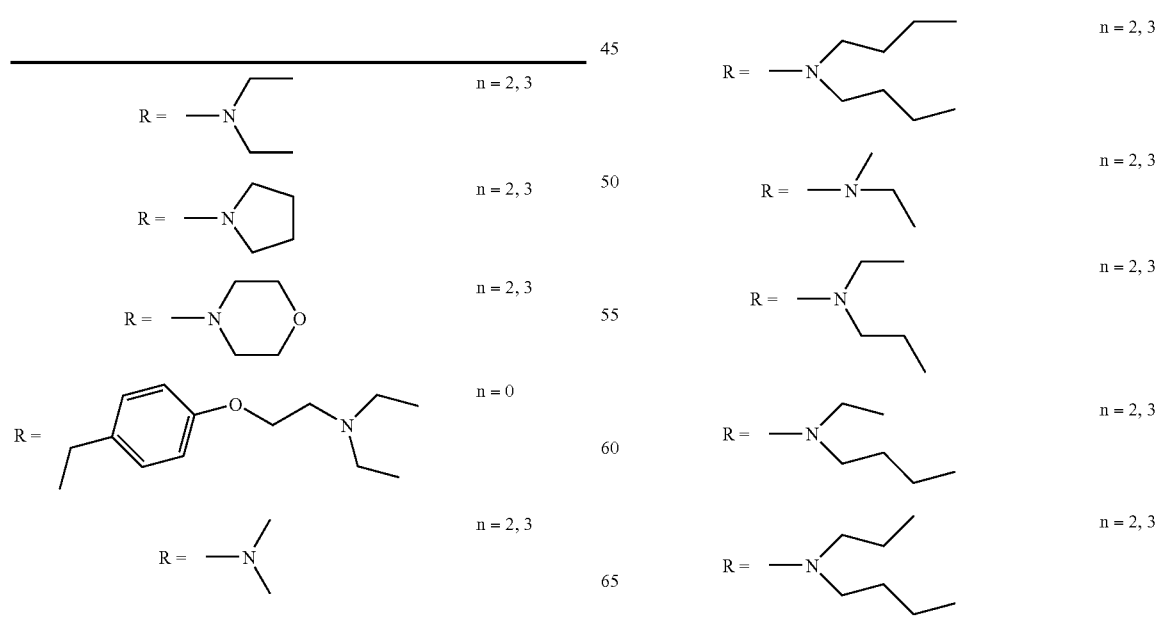

| | |
|---|---|
| R= —N(ethyl)(ethyl) | n = 2, 3 |
| R= —N(pyrrolidine) | n = 2, 3 |
| R= —N(morpholine) | n = 2, 3 |
| R= ethyl-phenyl-O-CH₂CH₂-N(ethyl)(ethyl) | n = 0 |
| R= —N(methyl)(methyl) | n = 2, 3 |

-continued

| | |
|---|---|
| R= —N(propyl)(propyl) | n = 2, 3 |
| R= —N(butyl)(butyl) | n = 2, 3 |
| R= —N(methyl)(ethyl) | n = 2, 3 |
| R= —N(ethyl)(propyl) | n = 2, 3 |
| R= —N(ethyl)(butyl) | n = 2, 3 |
| R= —N(methyl)(propyl) | n = 2, 3 |

-continued

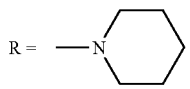

and physiologically acceptable salts, hydrates or solvates thereof.

4. The method according to one of preceding claims wherein the substituted sulphonamide is selected from the group consisting of:
N-(N,N-Diethylaminoethyl)benzene-1,4-bis(sulphonamide);
N-(N,N-Diethylaminopropyl)benzene-1,4-bis(sulphonamide);
N-(Pyrrolidinoethyl)benzene-1,4-bis(sulphonamide);
N-(Pyrrolidinopropyl)benzene-1,4-bis(sulphonamide);
N-(Morpholinoethyl)benzene-1,4-bis(sulphonamide);
N-(Morpholinopropyl)benzene-1,4-bis(sulphonamide);
N-(4-Diethylaminoethoxybenzyl)benzene-1,4-bis(sulphonamide);
N-(Dimethylaminoethyl)benzene-1,4-bis(sulphonamide);
N-(Dimethylaminopropyl)benzene-1,4-bis(sulphonamide);
N-(N,N-Dipropylaminoethyl)benzene-1,4-bis(sulphonamide);
N-(N,N-Dipropylaminopropyl)benzene-1,4-bis(sulphonamide);
N-(N,N-Dibuthylaminoethyl)benzene-1,4-bis(sulphonamide);
N-(N,N-Dibuthylaminopropyl)benzene-1,4-bis(sulphonamide);
N-(N-Methyl-N-ethylaminoethyl)benzene-1,4-bis(sulphonamide);
N-(N-Methyl-N-ethylaminopropyl)benzene-1,4-bis(sulphonamide);
N-(N-Ethyl-N-propylaminoethyl)benzene-1,4-bis(sulphonamide);
N-(N-Ethyl-N-propylaminopropyl)benzene-1,4-bis(sulphonamide);
N-(N-Ethyl-N-buthylaminoethyl)benzene-1,4-bis(sulphonamide);
N-(N-Ethyl-N-buthylaminopropyl)benzene-1,4-bis(sulphonamide);
N-(N-Propyl-N-buthylaminoethyl)benzene-1,4-bis(sulphonamide);
N-(N-Propyl-N-buthylaminopropyl)benzene-1,4-bis(sulphonamide);
N-(Piperidinoethy)benzene-1,4-bis(sulphonamide);
N-(Piperidinopropyl)benzene-1,4-bis(sulphonamide);
4-Sulfamoyl-N-(N,N-dimethylaminoethyl)benzamide;
4-Sulfamoyl-N-(N,N-dimethylaminopropyl)benzamide;
4-Sulfamoyl-N-(N,N-diethylaminoethyl)benzamide;
4-Sulfamoyl-N-(N,N-diethylaminopropyl)benzamide;
4-Sulfamoyl-N-(morpholinoethyl)benzamide;
4-Sulfamoyl-N-(morpholinopropyl)benzamide;
4-[N-(Morpholinopropyl)sulfamoyl]phenylsulfamoylbenzamide;
(N,N-Diethylaminoethyl)-4-sulfamoylbenzoate;
(N,N-Diethylaminopropyl)-4-sulfamoylbenzoate;
(N,N-Dipropylaminoethyl)-4-sulfamoylbenzoate;
(N,N-Dipropylaminopropyl)-4-sulfamoylbenzoate;
4-Sulfamoyl-N-(N,N-dipropylaminoethyl)benzamide;
4-Sulfamoyl-N-(N,N-dipropylaminopropyl)benzamide;
(N,N-Dibuthylaminoethyl)-4-sulfamoylbenzoate;
(N,N-Dibuthylaminopropyl)-4-sulfamoylbenzoate;
4-Sulfamoyl-N-(N,N-dibuthylaminoethyl)benzamide;
4-Sulfamoyl-N-(N,N-dibuthylaminopropyl)benzamide;
(N-Methyl-N-ethylaminoethyl)-4-sulfamoylbenzoate;
(N-Methyl-N-ethylaminopropyl)-4-sulfamoylbenzoate;
4-Sulfamoyl-N-(N-methyl-N-ethylaminoethyl)benzamide;
4-Sulfamoyl-N-(N-methyl-N-ethylaminopropyl)benzamide;
(N-Ethyl-N-propylaminoethyl)-4-sulfamoylbenzoate;
(N-Ethyl-N-propylaminopropyl)-4-sulfamoylbenzoate;
4-Sulfamoyl-N-(N-ethyl-N-propylaminoethyl)benzamide;
4-Sulfamoyl-N-(N-ethyl-N-propylaminopropyl)benzamide;
(N-Propyl-N-buthylaminoethyl)-4-sulfamoylbenzoate;
(N-Propyl-N-buthylaminopropyl)-4-sulfamoylbenzoate;
4-Sulfamoyl-N-(N-propyl-N-buthylaminoethyl)benzamide;
4-sulfamoyl-N-(N-propyl-N-buthylaminopropyl)benzamide;
(N-Ethyl-N-buthylaminoethyl)-4-sulfamoylbenzoate;
(N-Ethyl-N-buthylaminopropyl)-4-sulfamoylbenzoate;
4-Sulfamoyl-N-(N-ethyl-N-buthylaminoethyl)benzamide;
4-Sulfamoyl-N-(N-ethyl-N-buthylaminopropyl)benzamide;
(Pyrrolidinoethyl)-4-sulfamoylbenzoate;
(Pyrrolidinopropyl)-4-sulfamoylbenzoate;
4-Sulfamoyl-N-(pyrrolidinoethyl)benzamide;
4-Sulfamoyl-N-(pyrrolidinopropyl)benzamide;
(Piperidinoethyl)-4-sulfamoylbenzoate;
(Piperidinopropyl)4-sulfamoylbenzoate;
4-Sulfamoyl-N-(piperidinoethyl)benzamide; and
4-Sulfamoyl-N-(piperidinopropyl)benzamide.

5. A substituted sulphonamide having the general formula (I)

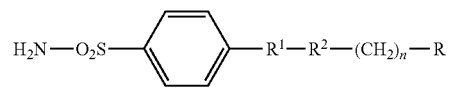

wherein
$R^1$ is $SO_2$,
$R^2$ is NH, and
R and n are shown in the following Table:

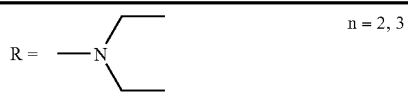

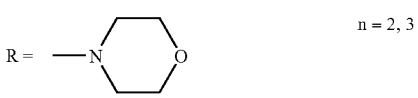

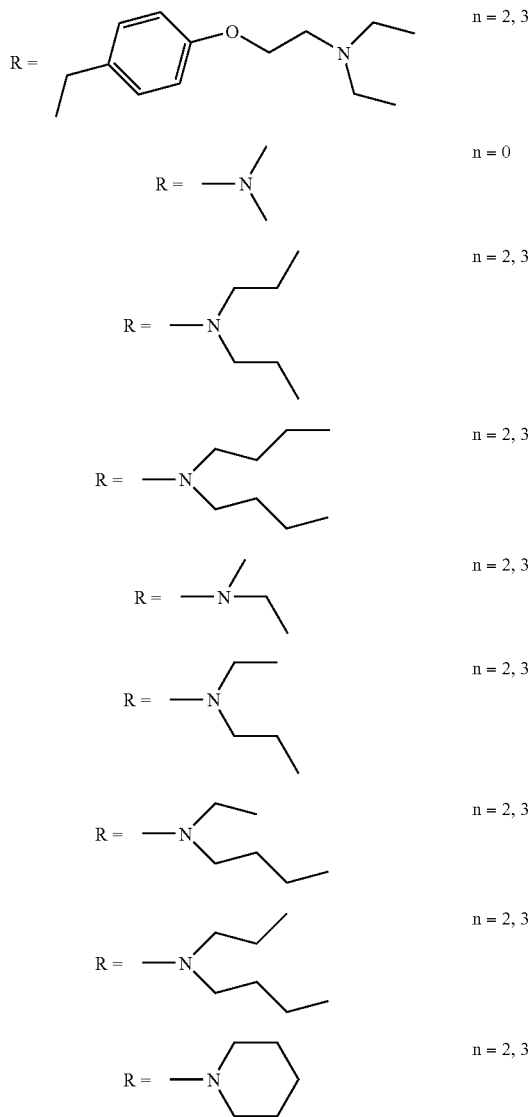

and physiologically acceptable salts, hydrates or solvates thereof.

6. A substituted sulphonamide having the general formula (I), according to claim 5,
which is selected from the group consisting of:
N-(N,N-Diethylaminoethyl)benzene-1,4-bis(sulphonamide);
N-(N,N-Diethylaminopropyl)benzene-1,4-bis(sulphonamide);
N-(Pyrrolidinoethyl)benzene-1,4-bis(sulphonamide);
N-(Pyrrolidinopropyl)benzene-1,4-bis(sulphonamide);
N-(Morpholinoethyl)benzene-1,4-bis(sulphonamide);
N-(Morpholinopropyl)benzene-1,4-bis(sulphonamide);
N-(4-Diethylaminoethoxybenzyl)benzene-1,4-bis(sulphonamide);
N-(Dimethylaminoethyl)benzene-1,4-bis(sulphonamide);
N-(Dimethylaminopropyl)benzene-1,4-bis(sulphonamide);
N-(N,N-Dipropylaminoethyl)benzene-1,4-bis(sulphonamide);
N-(N,N-Dipropylaminopropyl)benzene-1,4-bis(sulphonamide);
N-(N,N-Dibuthylaminoethyl)benzene-1,4-bis(sulphonamide);
N-(N,N-Dibuthylaminopropyl)benzene-1,4-bis(sulphonamide);
N-(N-Methyl-N-ethylaminoethyl)benzene-1,4-bis(sulphonamide);
N-(N-Methyl-N-ethylaminopropyl)benzene-1,4-bis(sulphonamide);
N-(N-Ethyl-N-propylaminoethyl)benzene-1,4-bis(sulphonamide);
N-(N-Ethyl-N-propylaminopropyl)benzene-1,4-bis(sulphonamide);
N-(N-Ethyl-N-buthylaminoethyl)benzene-1,4-bis(sulphonamide);
N-(N-Ethyl-N-buthylaminopropyl)benzene-1,4-bis(sulphonamide);
N-(N-Propyl-N-buthylaminoethyl)benzene-1,4-bis(sulphonamide);
N-(N-Propyl-N-buthylaminopropyl)benzene-1,4-bis(sulphonamide);
N-(Piperidinoethy)benzene-1,4-bis(sulphonamide); and
N-(Piperidinopropyl)benzene-1,4-bis(sulphonamide).

7. A substituted sulphonamide selected from the group consisting a sulphonamide of the general formula (I) according to claim 5 or 6, and physiologically acceptable salts, hydrates or solvates thereof, for use as antiglaucomatics.

8. A pharmaceutical composition for the prophylaxis and the treatment of diseases, characterized in that the pharmaceutical composition comprises an active ingredient selected from the group consisting of a substituted sulphonamide of the general formula (I) according to claim 5 or 6 and physiologic acceptable salts, hydrates or solvates thereof as the active compound, and a pharmaceutical carrier.

9. A pharmaceutical composition according to claim 8, characterized in that it additionally comprises a further active agent for the prophylaxis or the treatment of eye diseases and said futher active ingredient is selected from the group consisting of sympatomimetics, parasympatomimetics, betablocators, and prostagladine analougues, and other antiglaucomatics.

10. A process for preparing the compounds having the general formula (I) according to claim 5, characterized in that an amine of the general formula (IV)

$$H_2N-(CH_2)_n-R \qquad (IV)$$

wherein R is as defined in claim 5,
is treated with 4-sulfamoylbenzenesulphonyl chloride of the formula (V)

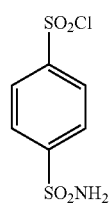

(V)

in organic solvent in the presence of a base excess at the temperature 0 to 20 ° C., wherein a nucleophilic reaction gives a substituted 1,4-bis sulphonamide.

11. A process according to claim 10, characterized in that tetrahydrofurane or ether are used as the organic solvents and triethylamine is used as the base.

12. A pharmaceutical composition according to claim 9, wherein the sympatomimetics are selected from the group consisting of brimonidine, clonidine and apraclonidine.

13. A pharmaceutical composition according to claim 9, wherein the parasympatomimetics are selected from the group consisting of pilocarpine and carbachole.

14. A pharmaceutical composition according to claim 9, wherein the betablocators are selected from the group consisting of timolol, betaxolol and levobunolol.

15. A pharmaceutical composition according to claim 9, wherein the prostagladine
analougues are latanoprost, bimaprost and travaprost.

16. A pharmaceutical composition according to claim 9, wherein the antiglaucomatics are selected from the group consisting of guanethidine and dapiprazole.

\* \* \* \* \*